United States Patent
Larsen et al.

(10) Patent No.: US 10,882,814 B2
(45) Date of Patent: Jan. 5, 2021

(54) METHOD FOR PRODUCING AN ESTER

(71) Applicant: PERSTORP AB, Perstorp (SE)

(72) Inventors: Magnus Larsen, Perstorp (SE); Susanne Stigsson, Perstorp (SE); Snjezana Trupina Grönlund, Kristianstad (SE); Christoffer Månsson, Örkelljunga (SE)

(73) Assignee: PERSTORP AB, Perstorp (SE)

( * ) Notice: Subject to any disclaimer, the term of this patent is extended or adjusted under 35 U.S.C. 154(b) by 241 days.

(21) Appl. No.: 16/097,662

(22) PCT Filed: Apr. 24, 2017

(86) PCT No.: PCT/SE2017/050398
§ 371 (c)(1),
(2) Date: Oct. 30, 2018

(87) PCT Pub. No.: WO2017/192084
PCT Pub. Date: Nov. 9, 2017

(65) Prior Publication Data
US 2020/0331838 A1   Oct. 22, 2020

(30) Foreign Application Priority Data
May 3, 2016 (SE) .................................. 1630101

(51) Int. Cl.
*C07C 67/08* (2006.01)
(52) U.S. Cl.
CPC .................................. *C07C 67/08* (2013.01)
(58) Field of Classification Search
CPC .................................................... C07C 67/08
See application file for complete search history.

(56) References Cited

U.S. PATENT DOCUMENTS

| 7,674,931 B1 | 3/2010 | O'Meadhra et al. |
| 2006/0051307 A1 | 3/2006 | Gotou et al. |
| 2011/0087044 A1 | 4/2011 | Weber et al. |

FOREIGN PATENT DOCUMENTS

| EP | 1199300 A2 | | 4/2002 |
| EP | 1327625 | * | 7/2003 |
| EP | 1327625 A1 | | 7/2003 |

OTHER PUBLICATIONS

International Search Report and Written Opinion dated Jun. 19, 2017 for corresponding PCT Application No. PCT/SE2017/050398.

* cited by examiner

*Primary Examiner* — Yevgeny Valenrod
*Assistant Examiner* — Blaine G Doletski
(74) *Attorney, Agent, or Firm* — Polsinelli PC

(57) ABSTRACT

Disclosed is a method for production of an ester obtained from a reaction between at least one alcohol having at least one hydroxyl group, such as a diol, and at least one linear of branched C3-C20 monocarboxylic acid, said reaction being performed in presence of at least one azeotropic solvent and optionally at least one antioxidant. Said method comprises the steps of (a) charging said alcohol, said monocarboxylic acid, and said azeotropic solvent and optionally said antioxidant to a reactor, (b) subjecting said alcohol and said carboxylic acid to esterification under reflux, (c) removing azeotropic solvent and unreacted carboxylic acid from yielded reaction mixture, (d) steam stripping off residual unreacted carboxylic acid, (e) neutralising yielded reaction product with an aqueous base, (f) separating water and organic phases, (g) recovering said organic phase and evaporating residual water, and (h) filtering off said antioxidant and possible remaining salts in yielded reaction product. The method is preferably performed in at least one reactor equipped with reflux, at least one vacuum pump, evaporation/distillation, steam stripping and decantation, and at least one filtration unit and optionally at least one coalescer filtre.

20 Claims, No Drawings

METHOD FOR PRODUCING AN ESTER

CROSS-REFERENCE TO RELATED APPLICATIONS

This application is a national stage application (under 35 U.S.C. § 371) of PCT/SE2017/050398, filed Apr. 24, 2017, which claims benefit of Swedish Application No. 1630101-2, filed May 3, 2016, which are incorporated herein by reference in their entireties.

The present invention refers to a method for production of an ester obtained from a reaction between at least one alcohol having at least one hydroxyl group and at least one linear of branched $C_3$-$C_{20}$ monocarboxylic acid, said reaction being performed in presence of at least one azeotropic solvent and at an carboxylic acid excess.

Linear and branched esters being the esterification or transesterification products of alcohols having one or more hydroxyl groups, such as mono, di, tri and polyols, and carboxylic acids or corresponding esters are well known in the art and typically used for several purposes, such as plasticisers and softening agents, lubricants, diluents and solvents, biofuels, fragrances and flavouring agents, as well as used in the manufacture of polymers, films, textiles, dyes, pharmaceuticals and cosmetics. Said linear and branched esters are extensively used in application fields such as films and sheets because they are excellent in transparency, mechanical strength, melting stability, solvent resistance and recyclability. Different sources of raw materials, such as molecular structure and purity of used alcohols and carboxylic acids, imply varying production processes to produce high quality esters.

The applications and production methods of said esters are well known in the art and do not require any further and over extensively detailed description. Said products are thoroughly disclosed and discussed in a number of chemical encyclopaedias and handbooks, such as Kirk-Othmer, Encyclopedia of Chemical Technology and Modern Polyesters: Chemistry and Technology of Polyesters and Copolyesters, ed. by John Scheirs and Timothy E. Long, 2003, John Wiley & Sons Ltd, ISBN 0-471-49856-4 and patents and patent applications, such as EP 1 199 300 teaching a method wherein an alcohol is reacted with a carboxylic acid in a presence of a Lewis acid catalyst in an amount of 0.00001 to 0.006 mol., RO 103976 referring to preparation of trieth-ylene glycol diacetate by esterification in the presence of acidic catalysts in a ratio 0.7 to 1.2% and US 2011/087044 disclosing a process for preparing polyol esters by reacting polyols with linear or branched aliphatic monocarboxylic acids in presence of an adsorbent, followed by removal of unreacted raw materials and subsequent steam treatment of resulting ester.

The present invention provides a novel and improved method for production of an ester obtained from a reaction between at least one alcohol having at least one hydroxyl group, such as a diol, and at least one linear of branched $C_3$-$C_{20}$ monocarboxylic acid, wherein said reaction is performed in presence of at least one azeotropic solvent, such as xylene, toluene and/or heptane and at a carboxylic acid excess and optionally in presence of at least one antioxidant, such as an alkali hypophosphite exemplified by, but not limited to, sodium hypophosphite.

The method according to the present invention comprises the steps of (a) charging at least one diol selected from the group consisting of a polyalkylene glycol and/or a 2,2-dialkyl-1,3-propanediol, at least one monocarboxylic acid selected from the group consisting of a 2-alkylhexanoic acid and/or a 2-alkylheptanoic acid, at least one azeotropic solvent, such as xylene, toluene and/or heptane, and optionally at least one antioxidant, such as an alkali hypophosphite, exemplified by, but not limited to, sodium hypophosphite, to a reactor, in carboxylic acid being charged in excess to said diol, such as 20-40% calculated as carboxylic groups on hydroxyl groups, (b) subjecting said diol and said carboxylic acid to esterification under reflux and at 220-250° C., said esterification being performed in absence of any catalyst (c) removing azeotropic solvent and unreacted carboxylic acid from yielded reaction mixture by vacuum evaporation/distillation, said evaporation/distillation being performed at 5-50 mbar and 150-210° C. and maintained until an acid value of <15 mg KOH/g is obtained, (d) steam stripping off residual unreacted carboxylic acid, said steam stripping being performed at 10-50 mbar and 150-210° C. and maintained until an acid value of <2 mg KOH/g, (e) neutralising at 50-100° C. yielded reaction product with an aqueous base, (f) separating water and organic phases, (g) recovering said organic phase and evaporating residual water at 20-40 mbar and 100-150° C., and (h) filtering off said antioxidant and possible remaining salts in yielded reaction product. Yielded reaction mixture after Step (e) and prior to Step (f) can suitably be allowed to pass through a coalescer filtre.

Said diol is in preferred embodiments diethylene glycol, triethylene glycol, neopentyl glycol, 2-ethyl-2-butyl-1,3-propanediol and/or 2-methyl-2-ethyl-1,3-propanediol and said monocarboxylic acid is in likewise preferred embodiments 2-ethylhexanoic acid and/or 2-propylheptanoic acid.

In various embodiments of the process according to the present invention is, said azeotropic solvent charged at 2-8%, such as 4-6%, by weight calculated on total reaction mixture and said antioxidant charged at 0.05-0.3% by weight calculated on total reaction mixture. In yet, further preferred embodiments, the reactor is purged with an inert gas, such as nitrogen and/or argon, during said esterification.

The present invention include embodiments wherein said Step (b) is performed at a temperature of 230-240° C. and at atmospheric pressure, said Step (c) is performed at 10-25 mbar and 170-190° C. until an acid value of <10 mg KOH/g is obtained, said Step (d) is performed at 20-40 mbar and 170-190° C. until an acid value of <1 mg KOH/g is obtained, said neutralisation in said Step (e) is performed using a 1-5%, such as 2-4%, aqueous solution of at least one alkali, such as potassium and/or sodium, hydroxide and/or carbonate, said Step (e) is performed at 80-95° C., said Step (f) is a phase separation performed by decantation and/or embodiments wherein recovered unreacted and/or excess carboxylic acid is recycled.

In especially preferred embodiments of the present invention is, said diol triethylene glycol, said monocarboxylic acid 2-ethylhexanoic acid and said yielded product triethyleneglycol-di-2-ethylhexanoate.

The method according to the present invention is suitably and preferably performed in at least one reactor equipped with reflux, at least one vacuum pump, evaporation/distillation, steam stripping and decantation, and at least one filtration unit and at least one coalescer filtre.

Without further elaboration, it is believed that one skilled in the art can, using the preceding description, utilise the present invention to its fullest extent. The following preferred specific embodiments are, therefore, to be construed as merely illustrative and not limitative of the remainder of the disclosure in any way whatsoever. In the following Examples 1 and 2 further illustrate the present invention, which is exemplified by embodiment methods producing triethyleneglycol-di-2-ethylhexanoate in embodiment equipment.

EXAMPLE 1

156 parts by weight of triethyleneglycol, 412 parts by weight of 2-ethylhexanoic acid, 23 parts by weight of xylene and 1.5 part by weight of sodium hypophosphite were charged to a reactor equipped with reflux, vacuum pump, evaporation/distillation, steam stripping and decantation. Triethyleneglycol and 2-ethylhexanoic acid was under reflux subjected to esterification at 235° C. and atmospheric pressure. The esterification time was 450 min. Xylene and excess/unreacted 2-ethylhexanoic acid were subsequent said esterification removed by applying vacuum and by evaporation/distillation at 20 mbar and 180° C. until an acid value of approx. 10 mg KOH/g was obtained. The reaction product was subsequent said evaporation/distillation, steam stripped at 25 mbar and 180° C. until an acid value of <1 mg KOH/g was obtained. Said steam stripping was followed by neutralisation of the reaction product using 3% aqueous sodium hydroxide followed by phase separation and decantation of the water and the organic phases. The organic phase was subsequently recovered and residual water was evaporated at 25 mbar and 120° C.

Obtained product was finally filtered in a filtration unit to remove sodium hypophosphite and possible salts.

Yielded product, triethyleneglycol-di-2-ethylhexanoate, exhibited the following properties:
Purity 98.3%
Acid value 0.06 mg KOH/g
Colour 15 APHA
Ash content 131 ppm (calculated as Na$^+$)

EXAMPLE 2

156 parts by weight of triethyleneglycol, 412 parts by weight of 2-ethylhexanoic acid, 23 parts by weight of xylene and 1.5 part by weight of sodium hypophosphite were charged to a reactor equipped with a reflux, vacuum pump, evaporation/distillation, steam stripping unit, coalescer filter and decantation. Triethyleneglycol and 2-ethylhexanoic acid was under reflux subjected to esterification at 235° C. and atmospheric pressure. The esterification time was 435 min. Xylene and excess/unreacted 2-ethylhexanoic acid were subsequent said esterification removed by applying vacuum and by evaporation/distillation at 20 mbar and 180° C. until an acid value of approx. 12 mg KOH/g was obtained. The reaction product was subsequent said evaporation/distillation steam stripped at 25 mbar and 180° C. until an acid value of <1 mg KOH/g was obtained. Said steam stripping was followed by neutralisation of the reaction product using 3% aqueous sodium hydroxide. Obtained neutralised mixture was allowed to pass through a coalescer filter followed by phase separation and decantation of the water and the organic phases. The organic phase was subsequently recovered and residual water was evaporated at 25 mbar and 120° C. Obtained product was finally filtered in a filtration unit to remove sodium hypophosphite and possible salts.

Yielded product, triethyleneglycol-di-2-ethylhexanoate, exhibited the following properties:
Purity 98.5%
Acid value 0.05 mg KOH/g
Colour 10 APHA
Ash content 86 ppm (calculated as Na$^+$)

The invention claimed is:

1. A method for producing an ester comprising:
    (a) charging a reactor with:
        at least one diol selected from a polyalkylene glycol and 2,2-dialkyl-1,3-propanediol,
        at least one carboxylic acid selected from a 2-alkylhexanoic acid and 2-alkylheptanoic acid,
        at least one azeotropic solvent, and
        optionally, at least one antioxidant,
        wherein the at least one carboxylic acid is charged in excess of the at least one diol;
    (b) subjecting the at least one diol and the at least one carboxylic acid to esterification under reflux at 220-250° C. in absence of any catalyst to derive a reaction mixture;
    (c) removing azeotropic solvent and unreacted carboxylic acid from the reaction mixture by vacuum evaporation/distillation at 5-50 mbar and 150-210° C. until an acid value of <15 mg KOH/g is obtained;
    (d) steam stripping off residual unreacted carboxylic acid from the reaction mixture at 10-50 mbar and 150-210° C. until an acid value of <2 mg KOH/g is obtained,
    (e) neutralizing the reaction mixture at 50-100° C. with an aqueous base,
    (f) separating the neutralized reaction mixture into water and an organic phase;
    (g) recovering the organic phase and evaporating any residual water from the organic phase at 20-40 mbar and 100-150° C., and
    (h) filtering off optional antioxidant and possible remaining salts to obtain the ester.

2. The method of claim 1, further comprising passing the neutralized reaction mixture of (e) through a coalescer filter prior to separating the neutralized reaction mixture into water and an organic phase in (f).

3. The method of claim 1, wherein the at least one diol is diethylene glycol, triethylene glycol, neopentyl glycol, 2-ethyl-2-butyl-1,3-propanediol, and/or 2-methyl-2-ethyl-1,3-propanediol.

4. The method of claim 1, wherein the at least one carboxylic acid is 2-ethylhexanoic acid and/or 2-propylheptanoic acid.

5. The method of claim 1, wherein the azeotropic solvent comprises xylene, toluene, and/or heptane.

6. The method of claim 1 comprising charging the reactor with at least one antioxidant selected from an alkali hypophosphite.

7. The method of claim 1, wherein the at least one carboxylic acid is charged in excess of 20-40% of the at least one diol, calculated as carboxylic groups on hydroxyl groups.

8. The method of claim 1, wherein the azeotropic solvent is charged at 2 to 8 wt. %, based on the total weight of the reaction mixture.

9. The method of claim 1, wherein the reactor is charged with 0.05 to 0.3 wt. % of antioxidants, based on the total weight of the reaction mixture.

10. The method of claim 1, wherein the reactor is purged with an inert gas during the esterification of (b).

11. The method of claim 1, wherein the at least one diol and the at least one carboxylic acid are subjected to esterification in (b) under reflux at 230-240° C.

12. The method of claim 1, wherein the esterification of (b) is performed at atmospheric pressure.

13. The method of claim 1, wherein the azeotropic solvent and unreacted carboxylic acid are removed from the reaction mixture of (c) by vacuum evaporation/distillation at 10-25 mbar and 170-190° C.

14. The method of claim 1, wherein the azeotropic solvent and unreacted carboxylic acid are removed from the reaction mixture of (c) by vacuum evaporation/distillation at 5-50 mbar and 150-210° C. until an acid value of <10 mg KOH/g is obtained.

15. The method of claim 1, wherein unreacted carboxylic acid is steam stripped off from the reaction mixture of (d) at 20-40 mbar and 170-190° C.

16. The method of claim 1, wherein unreacted carboxylic acid is steam stripped off from the reaction mixture of (d) until an acid value of <1 mg KOH/g is obtained.

17. The method of claim 1, wherein the reaction mixture is neutralized in (e) with an aqueous base selected from potassium hydroxide, sodium hydroxide, potassium carbonate, sodium carbonate, and a mixture thereof.

18. The method of claim 1, wherein recovering the organic phase and evaporating any residual water from the organic phase in (e) is carried out at 20-40 mbar and 100-150° C.

19. The method of claim 1, wherein the water and an organic phase are separated in (f) by decantation.

20. The method of claim 1, wherein the diol is triethylene glycol, the carboxylic acid is 2-ethylhexanoic acid, and the ester is triethyleneglycol-di-2-ethylhexanoate.

* * * * *